United States Patent [19]
Luchansky et al.

[11] Patent Number: 5,902,743
[45] Date of Patent: May 11, 1999

[54] PROBIOTIC BIFIDOBACTERIUM STRAIN

[75] Inventors: John B. Luchansky; Shu-Jean Tsai, both of Madison, Wis.

[73] Assignee: Wisconsin Alumni Research Foundation, Madison, Wis.

[21] Appl. No.: 09/045,332

[22] Filed: Mar. 20, 1998

[51] Int. Cl.$^6$ .............................. C12N 1/00; C12N 1/20; C12P 1/04; A01N 63/00
[52] U.S. Cl. ..................... 435/252.1; 435/822; 435/170; 435/252.9; 424/93.45
[58] Field of Search ............................... 435/252.1, 252.9, 435/822, 170; 424/93.45

Primary Examiner—Anthony C. Caputa
Assistant Examiner—John Weatherspoon
Attorney, Agent, or Firm—Quarles & Brady LLP

[57] ABSTRACT

Disclosed herein is a Bifidobacterium strain isolate. It can be used as an additive to infant food and beverage products, as well as to provide a healthful bacteria to human adults and non-human mammals. The bacterium acts as a probiotic. For example, the bacterium assists newborns in producing protective acetic acid and lactic acid, as well as antimicrobials and vitamins. The bacterium can also be used to reseed bacteria levels caused by diarrhea, chemotherapy, advancing age, antibiotics, or other causes.

1 Claim, No Drawings

PROBIOTIC BIFIDOBACTERIUM STRAIN

This invention was made with United States government support awarded by the following agencies: NSF Grant No: INT-9020678; USDA Grant No: 92-38500-7110; and USDA AGRICCREE Grant No: 91-37201-6762; HATCH #3360. The United States has certain rights in this invention.

BACKGROUND OF THE INVENTION

The present invention relates to use of a bacterial isolate as a probiotic.

There is a desire to provide women with the option to replace human breast milk with manufactured formula/foods. Research indicates that existing infant formula/foods do not provide certain of the protective benefits of human breast milk. For example, bifidobacteria species are constituents of the intestinal flora of infants. See generally R. Kok et al., 62 App. Env. Microb. 3668–3672 (1996); J.P. Langhendries et al., 21 J. Ped. Gastro. Nutr. 177–181 (1995). The disclosure of these publications and of all other publications referred to herein are incorporated by reference as if fully set forth herein.

Acetic acid and lactic acid production, as well as production of bacteriocins, other antimicrobials, and bioactive compounds, results from growth of Bifidobacterium and provides protective health benefits. Breast feeding appears to cause such bacteria to proliferate in human infants, albeit to date the mechanism by which this occurs has not been fully elucidated.

There have been proposals to add certain strains of bifidobacteria to animal feeds, and certain foods and beverages intended for humans. See J. Luchansky, 67 Ped. Basics 2–7 (1994); J. Reiter, Dairy Foods, p. 26 (March 1994); D. Hughes et al., 45 Food Tech. 74–83 (1991); U. Dubey et al., 79 J. Dairy Sci. 1146–1163 (1996).

With respect to human infants it has not previously been known where and how newborn infants acquire the bifidobacteria which are the most desirable for them, which particular strain(s) of Bifidobacterium are the most beneficial when the infant is the most vulnerable, and whether key strain(s) have yet to be isolated. Thus, to date infant formulas/baby foods have not proved to be sufficiently good substitutes for human breast milk with respect to Bifidobacterium.

Also of concern is the need to provide protective affects for non-human animals, such as by pretreating feeds with desirable bacteria, including bifidobacteria.

Another area of concern relates to humans who have diminished levels of desirable bacteria in their gut for reasons other than being newborns (e.g. due to diarrhea, chemotherapy, antibiotic treatment, or advanced age). Foods, beverages, oral treatments or other probiotic techniques for providing desirable bacteria to humans are therefore of interest.

BRIEF SUMMARY OF THE INVENTION

The invention provides a Bifidobacterium strain designated as American Type Culture Collection (ATCC) #202078, in a form separate from a live human (e.g. an isolate). A sample has been deposited with the American Type Culture Collection, 10801 University Boulevard, Manassas, Va. 20110-2209 on Jan. 9, 1998 with that Accession Number, under the conditions of the Budapest Treaty. This deposit does not imply or grant a license to use the bacterium. A taxonomic description of the bacterium is *Bifidobacterium longum* JBL 28-1/3300.

The invention also provides a food, beverage, dietary supplement, or animal feed containing this Bifidobacterium strain. Such foods, beverages, supplements, and feeds are designed to act as probiotics when fed orally or otherwise to humans (e.g. infants) by "seeding" the gut with the bacterial strain.

In its simplest form, the strain can be orally fed to a human (preferably an infant) in liquid form. It can be separately swallowed, or included in newborn vitamin preparations or the like. It can also be provided in tablets or capsules for ingestion as a dietary aid or supplement.

Alternatively, the bacterium can be included in a beverage suitable for humans (especially newborns), such as infant formula, fermented milk and fruit juice.

Preferred food items that can be inoculated with the bacterium are dairy products (such as cheese, yogurt, and ice cream). Other inoculated foods such as cereals, fruits and/or vegetables (such as strained apple sauce and carrots and peas) are also suitable for this invention.

In an alternative form, animal grains such as corn and soy can be inoculated with the bacterium and then fed to swine, poultry, or other non-human mammals.

The objects of the present invention therefore include providing:

(a) a bacterial strain type that produces acetic acid, lactic acid, bacteriocins, and/or antimicrobials in a mammalian (preferably human infant) gut;

(b) a beverage/food/feed which can simulate certain important protective effects of breast milk; and (c) an isolated form of a bacteria which is protective for newborn humans and both normal and health-compromised adults.

These and still other objects and advantages of the present invention will be apparent from the description which follows. The following description is merely of the preferred embodiments. Thus, the claims should be looked to in order to understand the full scope of the invention.

DETAILED DESCRIPTION

General Overview

We took 196 human samples from a family (mother, infant, father, sibling). Fecal samples (especially from the newborn infant and her sibling) were found to be the major source of bifidobacteria. Importantly, no bifidobacteria were found in 6 breast milk samples tested from the mother.

A Bifidobacterium strain was found in oral and nasal samples taken from the infant immediately after birth, but not from these same sources when sampled later on the same day. In contrast, no Bifidobacterium strain was recovered from 11 fecal and 6 vaginal samples within the first 37 hours, but a specific Bifidobacterium strain was recovered from infant fecal samples obtained from $\geq 38$ hours to 1 year after birth. Bifidobacteria were detected in all 11 infant samples obtained at 6 months, but only in 4 out of the 13 samples obtained at 12 months.

Genomic fingerprinting via pulsed field gel electrophoresis (PFGE) was conducted on intact genomic DNA from 16 Bifidobacterium strains from the newborn female obtained from 6 positive samples (2 each from mouth, nose, and anus) taken immediately after birth and 1 fecal isolate from the second day (38 h). All 17 isolates recovered from the 7 positive samples displayed essentially the same restriction fragment genomic fingerprints. Essentially the same fingerprint elements were also observed in all 6 Bifidobacterium strains recovered from 2 fecal samples obtained from the mother at the time of birth. Maternal feces (not breast milk) was therefore the source of the Bifidobacterium found in the neonate. Since the breast milk itself did not have the bacteria, breast milk appears to be a prebiotic, not a probiotic.

Bifidobacterium strains otherwise obtained from the infant within 1 month, at 6 months and up to 3 years after delivery were also analyzed. Isolates recovered from the infant samples taken from delivery to 1 month belonged to a single clonal type. However, isolates recovered from samples obtained at 6 months after birth contained three clonal types. Clonal type A was the predominant group observed in isolates from positive samples from delivery to 1 month. It was also present in bifidobacteria at six months, but was not the predominant group at 6 months.

Between 1 month and 6 months the infant was fed solid foods and received some antibiotics. Thus, the different diet and/or medicine is suspected to have caused subtle changes in the flora that were only discoverable via the conduct of PFGE.

In addition to 6 isolates recovered from 2 fecal samples taken from the mother at the time of birth, isolates from 3 fecal samples obtained within 1 month after delivery also displayed the same or closely related genomic fingerprints to that which predominated in the breast fed child. In contrast, 5 isolates from one vaginal sample and another 2 fecal samples taken from the mother at the same period showed distinct genomic fingerprints. Also, isolates from the mother's fecal is samples taken at 6 and 12 months displayed significantly different fingerprints.

These data indicated that a particular clone of bifidobacterium predominated in this mother at parturition, and, thereafter, became much less prevalent. Isolation of this Bifidobacterium clone from a healthy infant throughout the first 12 months is indicative of the safe nature of this bacterium in vivo. Its predominance when the infant is youngest (and thus most vulnerable) suggests its importance.

We therefore chose this strain for the ATCC deposit referred to above, and for use as a probiotic. The genomic fingerprint of this strain did not match the genomic fingerprint of any of the known Bifidobacterium strains that we tested.

Isolation

As noted above, we obtained samples from a newborn infant (e.g. feces). We cultured the sample overnight at 37° C. in Reinforced Clostridal medium, plus 0.5% propionic acid and 0.05% cysteine-HCl (pH 5.0)(RC5 medium) under anaerobic conditions. We then streaked portions therefrom onto RC5 agar plates, and then incubated the plates 2–3 days at 37° C. under anaerobic conditions.

We then selected milky white, large colonies for further characterization and placed them in Brain Heart Infusion (BHI) broth supplemented with 0.5% yeast extract, 0.5% dextrose and 0.05% cysteine-HCl. A representative colony was selected and submitted for the previously mentioned ATCC deposit.

EXAMPLES

A preferred beverage of the present invention is infant formula such as Carnation Good Start (Nestle Nutrition Division; Glendale, Calif.) that has been inoculated with the bacterium. The bacterium can also be introduced into various other beverages suitable for humans, especially infants and toddlers. Examples could include, but not be limited to, fluid milks such as Nutrish A/B produced by Mayfield Dairy Farms (Athens, Tenn.), fermented milks such as kefir produced by Lifeway Foods (Skokie, Ill.), and/or yogurts such as Mil—Mil produced by Yakult (Japan). Other bifid-amended beverages could include fruit juices and/or sports drinks.

Preferred food items that can be inoculated with the bacterium include dairy-based products such as natural cheese, cottage cheese, and ice cream. Fruits and vegetables targeted for infants/toddlers, such as apple sauce or strained peas and carrots (Gerber Products Company; Fremont, Mich.) are also suitable for inoculation. Both infant cereals such as rice-or oat-based cereals (Gerber) and adult cereals such as Musilix may also be suitable for this invention. In addition to foods targeted for human consumption, animal feeds may also be suitable for inoculation. It may also be of benefit to directly inoculate newborn humans or animals with a solution containing the preferred strain and to continue to dose such individuals with this strain at regular intervals throughout weaning and during periods of stress, diarrhea, and transit.

For some applications, it may be advantageous to also encapsulate the bacterium to better deliver, distribute, and/or protect it in foods/beverages. Likewise, it may be advantageous to include bifidogenic factors (i.e., pre-biotics) along with the bifidobacteria (i.e., pro-biotics) in the above mentioned foods, feeds, and supplements. When used together in a food, feed, or supplement, the combination of a pro-biotic and a pre-biotic is referred to as a synbiotic. Bifidogenic factors would include, but not be limited to, fructoligosaccharides such as Raftilose (Rhone-Poulenc, Cranbury, N.J.), inulin (Imperial Holly Corp., Sugar Land, Tex.), and Nutraflora (Golden Technologies, Westminister, Colo.), as well as xylooligosaccharides, galactooligosaccharides, soyoligosaccharides, lactulose/lactitol, etc.

A particularly suitable baby formula/food can be prepared by supplementing a powdered formula such as Carnation Good Start with about $10^6$ colony forming units (CFU) of Bifodobacterium ATCC 202078 per gram of powder. Alternatively, the bifidobacteria may be encapsulated prior to the addition to the formula and/or the formula could also contain bifidogenic factors at levels adequate to deliver 10 to 15 grams of pre-biotic per day. The amended formula can then be rehydrated with water as per the manufacturers instructions (for formula absent the bacteria), and refrigerated for at least 24 hours.

Likewise, strain ATCC 202078 could be added to cheese milk at levels of $10^6$ cfu per milliliter as a starter adjunct in the manufacture of Cheddar cheese. It is also envisioned that the bifidobacteria could be blended into yogurt (e.g. frozen yogurt) or kefir to achieve levels of at least $10^6$ cfu per gram. It may also be incorporated into tablets or capsules for sale as a digestion aid or dietary supplement.

One could also inoculate standard animal feed (e.g. pig feed) with this bacteria, with or without a pre-biotic. We did this with pig feed (along with three other strains of bacteria). The treated feed was fed to newborn piglets and the progress of the piglets were monitored. The piglets showed appropriate weight gain and other characteristics, notwithstanding being subjected to the bacteria.

Industrial Application

The invention provides improved beverages, foods, and feeds, and other products for increasing levels of healthful bacteria in mammalian guts.

We claim:

1. An isolated Bifidobacterium, wherein said Bifidobacterium is a Bifidobacterium having American Type Culture Collection designation ATCC#202078.

* * * * *